United States Patent

Tabota et al.

[11] Patent Number: 6,043,588
[45] Date of Patent: Mar. 28, 2000

[54] PIEZOELECTRIC SENSOR AND ACCELERATION SENSOR

[75] Inventors: Jun Tabota, Toyama-ken; Mitsugu Ogiura, Toyama; Toshihiko Unami, Toyama-ken, all of Japan

[73] Assignee: Murata Manufacturing Co., Ltd., Japan

[21] Appl. No.: 08/683,231

[22] Filed: Jul. 18, 1996

[30] Foreign Application Priority Data

| Jul. 18, 1995 | [JP] | Japan | 7-181675 |
| Jul. 27, 1995 | [JP] | Japan | 7-191588 |
| Aug. 29, 1995 | [JP] | Japan | 7-220334 |

[51] Int. Cl.⁷ .................................................. H01L 41/08
[52] U.S. Cl. ..................... 310/329; 310/328; 310/332; 310/348; 310/366
[58] Field of Search .................... 310/354, 328, 310/333, 344, 329, 332, 348, 366, 367, 368

[56] References Cited

U.S. PATENT DOCUMENTS

| 3,113,223 | 12/1963 | Smith et al. | 310/329 |
| 4,051,395 | 9/1977 | Taylor | 310/329 |
| 4,485,325 | 11/1984 | Yamamoto et al. | 310/344 |
| 4,489,609 | 12/1984 | Burdess et al. | 310/329 X |
| 5,128,581 | 7/1992 | Nakayama et al. | 310/329 |
| 5,235,237 | 8/1993 | Leonhardt | 310/329 |
| 5,388,459 | 2/1995 | Inoue et al. | 310/329 X |
| 5,392,006 | 2/1995 | Ikeda et al. | 331/158 |
| 5,408,878 | 4/1995 | Lysen | 73/517 R |
| 5,430,345 | 7/1995 | Takahashi | 310/348 |
| 5,515,725 | 5/1996 | Tabota et al. | 310/321 X |
| 5,532,542 | 7/1996 | Yoshida et al. | 310/348 |
| 5,539,270 | 7/1996 | Kaji | 310/329 |
| 5,589,724 | 12/1996 | Satoh et al. | 310/348 |
| 5,596,243 | 1/1997 | Tsuru et al. | 310/348 |

FOREIGN PATENT DOCUMENTS

| 0616221 | 9/1994 | European Pat. Off. . |
| 0616222 | 9/1994 | European Pat. Off. . |

Primary Examiner—Mark O. Budd
Attorney, Agent, or Firm—Ostrolenk, Faber, Gerb & Soffen, LLP

[57] ABSTRACT

A piezoelectric sensor has a piezoelectric element having a specific axis of sensitivity and a package for the piezoelectric element. The package has a rectangular parrallelopiped configuration with opposite longitudinal end surfaces having a height-to-width ratio of about 1:1. External lead electrodes are formed to cover at least the longitudinal end surfaces. A method and apparatus for detecting if the sensor is disposed in the proper posture is also disclosed.

3 Claims, 8 Drawing Sheets

PIEZOELECTRIC SENSOR AND ACCELERATION SENSOR

BACKGROUND OF THE INVENTION

1. Field of the Invention

The present invention relates to a piezoelectric sensor for sensing acceleration or vibration and, more particularly, to a piezoelectric sensor to be mounted on a substrate such as a printed circuit board.

2. Description of the Related Art

An acceleration sensor which is a kind of piezoelectric sensor is usually used by packaging it or mounting it on a mounting substrate such as a circuit board which has a circuit for processing acceleration signals generated by the sensor.

Mounting of an acceleration sensor on a mounting substrate has caused two major problems in the prior art.

The first problem is as follows. The design of an acceleration sensor to be mounted on a substrate is made such that the sensor senses acceleration acting in directions perpendicular to the plane of the mounting substrate or acceleration acting parallel to the plane of the mounting substrate, depending on factors such as the use of the sensor and specifications of the circuit board. It is therefore necessary that the acceleration sensor be mounted on the circuit board so as to be sensitive to acceleration acting in either one of the above-mentioned directions.

Meanwhile, the acceleration sensor has a rectangular parallelopiped configuration having six surfaces, and is adapted to be jointed to the circuit board at a specific one of the six surfaces or a surface opposite to this surface. This is because the acceleration sensor has a flattened rectangular parallelopiped configuration having a rectangular bottom and top surfaces and side surfaces of a height which is small as compared with the two sides of the rectangle comprising the top and bottom surfaces, so that the sensor can be soldered to the circuit board while being stably held on the circuit board. For instance, the height ranges from 0.5 to 0.7 times as large as the length of the shorter side of the rectangle defining the top and bottom surfaces.

Consequently, it has been necessary to prepare two types of acceleration sensors: an acceleration sensor of the type which is capable of sensing acceleration acting perpendicularly to the plane of the circuit board and an acceleration sensor of the type which is capable of sensing acceleration acting parallel to the plane of the circuit board. An acceleration sensor of either one of these two types is selected for use. This not only raises the costs of production of acceleration sensors but also requires costs for storing and administrating these two types of acceleration sensors, resulting in a rise in the costs of various products incorporating such acceleration sensors.

The second problem is as follows: The circuit board on which an acceleration sensor is packaged may be deflected for any reason, before or after the packaging of the acceleration sensor. specifically, the deflection of the circuit board causes a corresponding deformation of the acceleration sensor. Such a deformation of the acceleration sensor due to an external force adversely affects the piezoelectric member which senses acceleration, thus hampering sensing of acceleration. This problem is particularly serious when the acceleration sensor is intended to sense acceleration acting perpendicularly to the plane of the mounting substrate, because in such a case the direction of acceleration to be sensed coincides with the direction of deflection of the mounting substrate. Consequently, the acceleration sensor may be influenced by the deflection of the circuit board so as to erroneously produce an acceleration signal even when there is no acceleration acting on the sensor.

SUMMARY OF THE INVENTION

Accordingly, an object of the present invention is to provide a piezoelectric sensor which can reduce adverse effects due to the deflection of the substrate and a piezoelectric sensor which can be mounted on a circuit board selectively either in a direction to sense acceleration perpendicular to the plane of the circuit board or in a direction to sense acceleration parallel to the plane of the circuit board, thereby obviating at least one of the two major problems encountered with the prior art.

To this end, according to one aspect of the present invention, there is provided a piezoelectric sensor comprising: a piezoelectric element having a specific axis of sensitivity; and a package in which the piezoelectric element is packaged; wherein the package has a rectangular parallelopiped configuration with end surfaces having a height-to-width ratio approximating 1:1, and wherein external lead electrodes are formed on at least the end surfaces.

According to a second aspect of the present invention, there is provided an acceleration sensor comprising: a bimorph element having an axis of highest sensitivity extending in a direction which substantially coincides with a line normal to the plane of a circuit board; and a case assembly for fixing and supporting both longitudinal ends of the bimorph element, the case assembly being adapted to be mounted on the circuit board at both its longitudinal ends which support both longitudinal ends of the bimorph element; wherein the bimorph element has a pair of piezoelectric ceramic plates each having a signal electrode and an intermediate electrode formed on the opposite major surfaces thereof, the piezoelectric ceramic plates being joined to each other face to face at their surfaces having the intermediate electrodes such that the intermediate electrodes are coupled to each other; each of the piezoelectric ceramic plates being sectioned in the longitudinal direction of the bimorph element into three sections including a central section and both end sections at border lines which are positioned such that when the bimorph element is deformed in response to deflection of the circuit board, the quantity of charges generated in the central section equals the sum of the quantities of the charges generated in both the end sections, the central section and both end sections of each piezoelectric ceramic plates being polarized thicknesswise of the piezoelectric ceramic plate in opposite directions, the directions of polarization of the central section and both end sections of one of the piezoelectric ceramic plates being opposite to those of the other of the piezoelectric ceramic plates.

According to a third aspect of the present invention, there is provided an electronic part having a polyhedral body on opposing end surfaces of which are formed electrodes for outputting voltages of different polarities, the electronic part comprising: a conductive film formed on one of the surfaces of said body orthogonal to the end surfaces having the electrodes at a predetermined position closer to one of the end surfaces than to the other, the conductive film having an area large enough to be simultaneously contacted by a pair of probe terminals for applying a voltage.

According to a fourth aspect of the present invention, there is provided a method of examining posture of an electronic part which has to be placed in a predetermined posture in terms of up and down, left and right and front and back directions, the method comprising: bringing a pair of probe terminals into contact with a potion of an upwardly directed surface of the electronic part disposed in an examination position in an arbitrary posture, the portion being closer to one of the end surfaces having electrodes than to the other; applying a voltage between the probe terminals; and determining, based on the presence or absence of electrical current between the probe terminals, whether the electronic part as the examination object has been placed in a correct posture.

According to a fifth aspect of the invention, there is provided an apparatus for examining posture of an electronic part and which has to be placed in a predetermined posture in terms of up and down, left and right and front and back directions, the apparatus comprising: a pair of probe terminals adapted to be brought into contact with a potion of an upwardly directed surface of the electronic part disposed in an examination position in an arbitrary posture, the portion being closer to one of the end surfaces having electrodes than to the other; detecting means for applying a voltage between the probe terminals and for detecting presence or absence of electrical current between the pair of probe terminals; and determining means for determining, based on the results of the detection by the detecting means, whether the electronic part as the examination object has been placed in a correct posture.

The piezoelectric sensor in accordance with the present invention is designed to be stably seated on a printed circuit board regardless of the posture of mounting thereof on the printed circuit board. Therefore, a single piezoelectric sensor can provide a variety of directions of axis sensitivity, by changing the posture of the piezoelectric sensor mounted on the printed circuit board, thus widening the adaptability of the piezoelectric sensor. The present invention therefore achieves a remarkable reduction in the costs of production and management of piezoelectric sensors and, hence, the price of the same.

The acceleration sensor of the present invention offers an advantage in that, even if the bimorph element is deformed due to the influence of deflection of the circuit board on which the acceleration sensor is mounted, charges generated as a result of the deformation are canceled by each other, so that no signal charges are derived from the sensor when no acceleration is acting thereon, whereby the influence of deflection of the circuit board is eliminated. However, when acceleration acts on the acceleration sensor, charges are generated in the central section and both end sections of each piezoelectric ceramic plate, based on the relationship between the directions of polarization of these sections and the tensile and compression stresses caused by the deformation. Such charges are picked up as output signal voltage, without being canceled, thus providing a high level of output signal. According to the invention, therefore, it is possible to suppress influence caused by deflection of the circuit board, while achieving a higher degree of reliability. Moreover, a high level of sensor output can be obtained when acceleration actually acts on the sensor.

The electronic part in accordance with the present invention enables, with simple electronic processing, confirmation of the posture of the electronic part which is to be mounted on a printed circuit board or to be loaded in a tape carrier correctly in a predetermined posture, with a high degree of accuracy while avoiding increase in production cost.

The examination method and apparatus of the present invention enables the confirmation of the electronic part under the condition described above. In particular, the examination apparatus offers a remarkable reduction in the installation cost as compared with the conventional examination system which relies upon image processing techniques.

The above and other objects, features and advantages of the present invention will become clear from the following description of the preferred embodiments when the same is read in conjunction with the accompanying drawings.

DESCRIPTION OF PREFERRED EMBODIMENTS

First Embodiment

Figure 1:
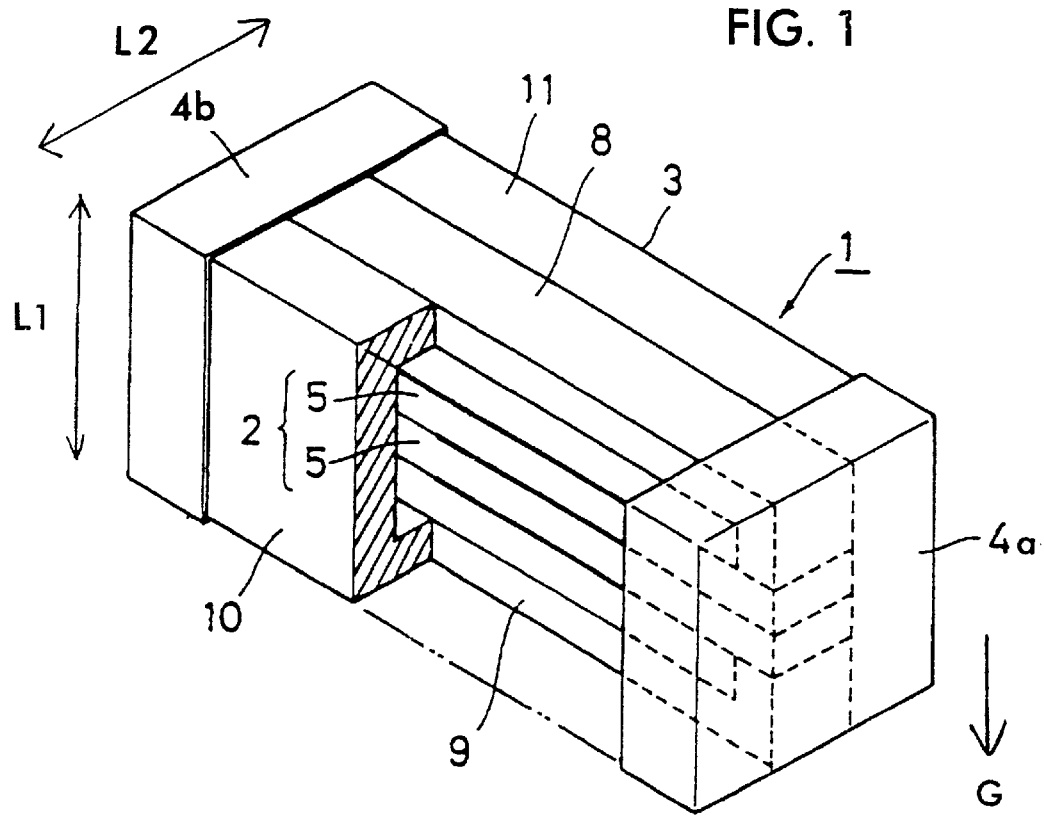
FIG. 1 is a partly-sectioned perspective view of an embodiment of the acceleration sensor in accordance with the present invention.
Figure 3:
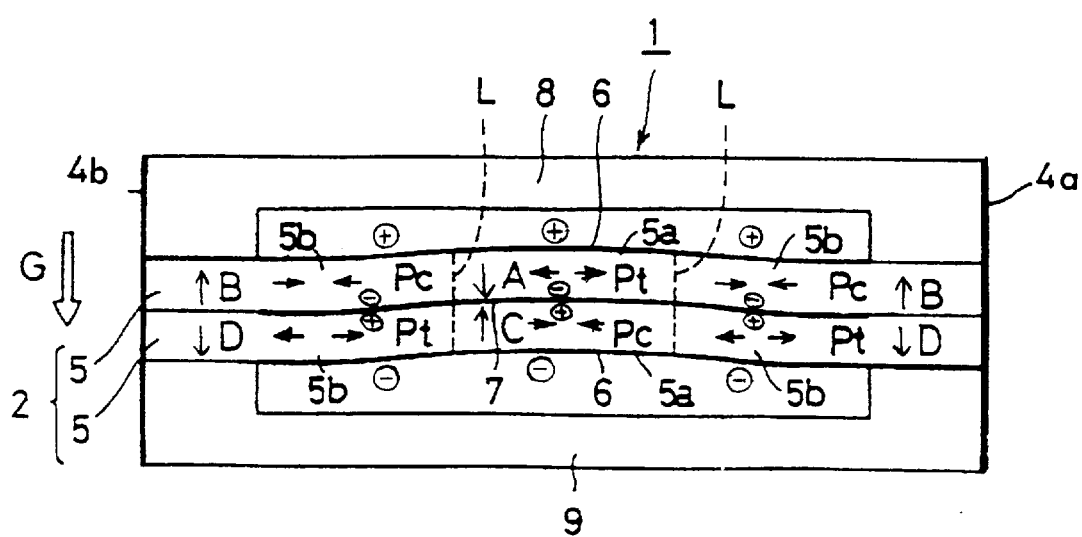
FIG. 3 is a schematic illustration of a piezoelectric element deformed under action of acceleration.
Figure 2:
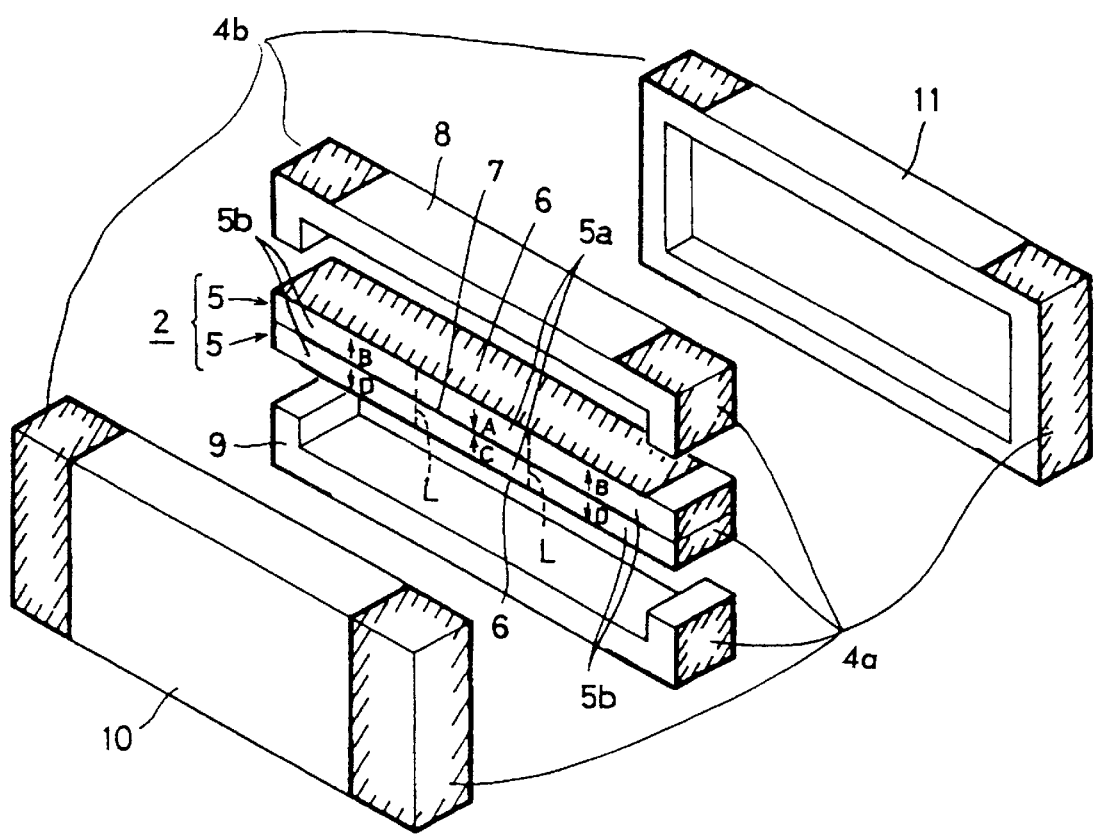
FIG. 2 is an exploded perspective view of the acceleration sensor as shown in FIG. 1.
Figure 4A:
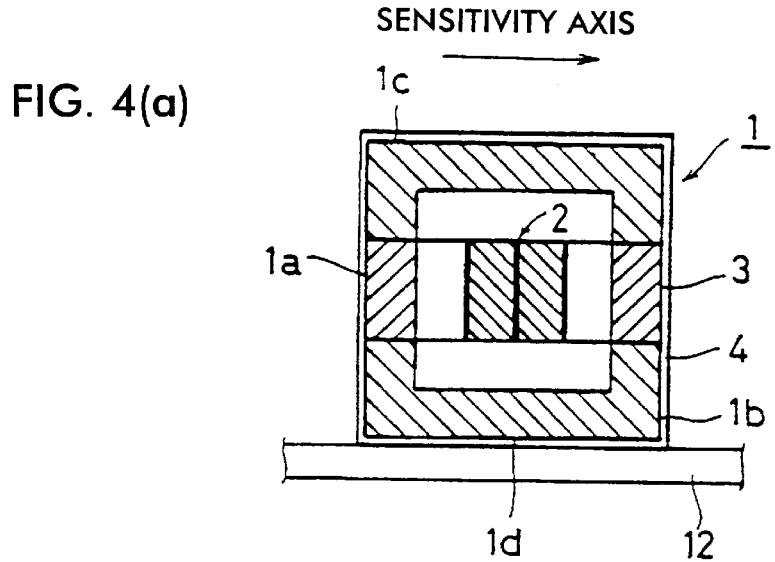
FIGS. 4(a) and 4(b) are illustrations of the postures in which the acceleration sensor of FIG. 1 is mounted on a printed circuit board.
Figure 4B:
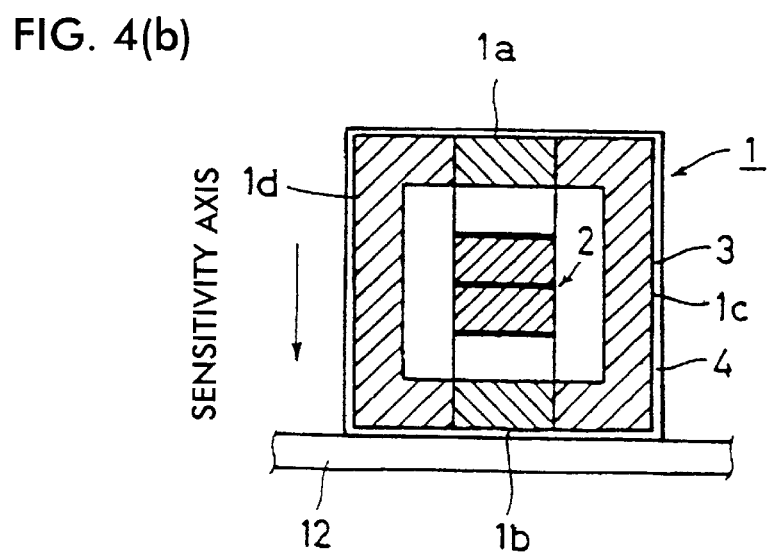
Figure 5:
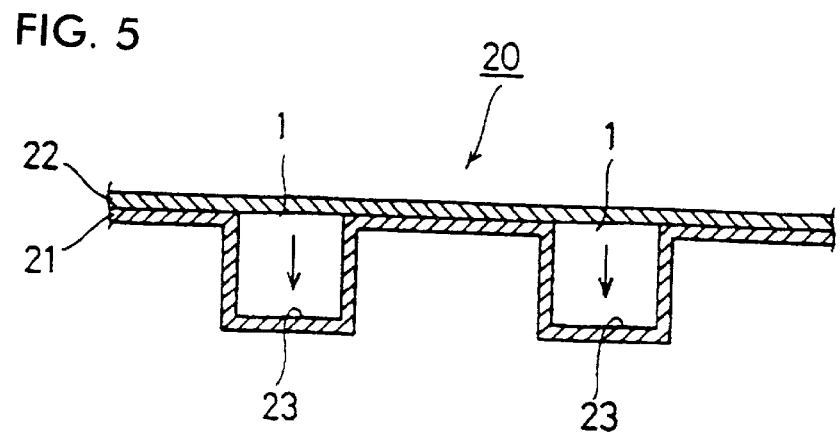
FIG. 5 is an illustration of the acceleration sensor of FIG. 1 carried by a tape carrier.
Figure 6:
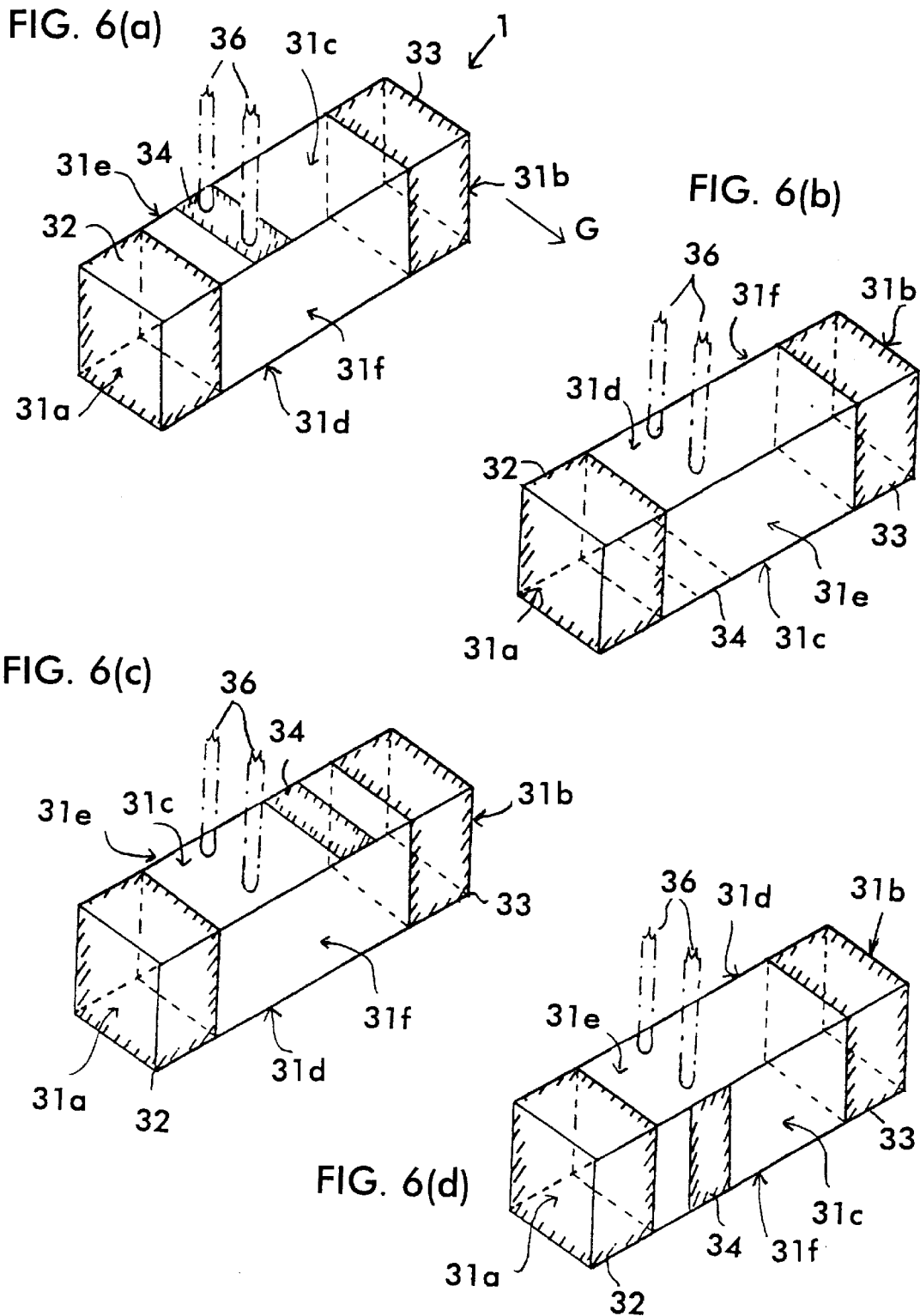
FIGS. 6(a) to 6(d) are perspective views of a second embodiment of the acceleration sensor in accordance with the present invention, showing positioning of the sensor relative to probe terminals.

A first embodiment of a piezoelectric sensor of the present invention, serving as an acceleration sensor sensitive to acceleration, will be described with specific reference to FIGS. 1 to 5. FIG. 1 is a partly-sectioned perspective view of an embodiment of the acceleration sensor in accordance with the present invention. FIG. 2 is an exploded perspective view of the acceleration sensor as shown in FIG. 1. FIG. 3 is a schematic illustration of a piezoelectric element deformed under action of acceleration. FIGS. 4(a) and 4(b) are illustrations of the postures in which the acceleration sensor is mounted on a printed circuit board. FIG. 5 is an illustration a tape carrier carrying the acceleration sensor.

Referring to these Figures, an embodiment of the acceleration sensor 1 has a piezoelectric element 2 of a type known as a "bimorph piezoelectric element", a package 3 and external leads 4a, 4b. The acceleration sensor 1 has a sensitivity axis which, as indicated by an arrow, extends in the direction of thickness according to a definition given later of the piezoelectric element 2.

The piezoelectric element 2 has a pair of strip-shaped piezoelectric ceramic plates 5, 5 each having on its major surfaces a signal pickup electrode 6 and an intermediate electrode 7, the piezoelectric ceramic plates 5, 5 being jointed face to face at their intermediate electrodes 7, 7. The direction of stacking of the pair of piezoelectric ceramic plates 5, 5 is referred to as the direction of thickness of the piezoelectric element 2. Each of the piezoelectric ceramic plates 5, 5 is divided in the longitudinal direction into three sections 5a, 5b and 5b at border lines L, L. The arrangement is such that a tensile stress or a compression stress acts on each section 5a, 5b, 5b in response to acceleration G acting on the sensor. The central sections 5a and both end sections 5b of both piezoelectric ceramic plates 5, 5 are polarized in opposite directions along the thicknesses of the piezoelectric ceramic plates 5, as indicated by arrows A, B and C, D. More specifically, the central sections 5a, 5a are polarized towards each other as indicated by the arrows A and C, whereas both end sections 5b, 5b; 5b, 5b are polarized away from each other, as indicated by the arrows B and D.

The package 3 has a pair of clamping members 8, 9 each having a substantially square-bottomed U-like form when viewed from one side thereof, for clamping each longitudinal end portion of the piezoelectric element 2 from the upper and lower sides of the piezoelectric element 2. The package 3 also has a pair of cover members 10, 11 each having a substantially squarebottomed U-shaped cross-section, the cover members 10, 11 being secured to the left and right ends of the clamping members 8, 9 so as to cover the left and right side faces of the piezoelectric element 2. The package 3 generally has a rectangular parallelopiped configuration, with opposing end surfaces having a height-to-width ratio of 1:1 i.e., a square configuration. Representing the height and the width of the end surface by L1 and L2 (FIG. 1), respectively, according to the present invention, it is preferred that the ratio L1/L2 is set to about 1.0, i.e., to meet the condition of L1=L2, although the invention does not exclude such a height-to-width ratio L1/L2 of from about 0.9 to 1.1.

In accordance with the present invention, the external lead electrodes 4a, 4b are provided in the form of layers laid on the longitudinal end surfaces of the package 3 including the longitudinal end surfaces of the piezoelectric element 2. One of the external lead electrodes 4a, 4b is connected to one of the signal pickup electrodes 6, 6 formed on the piezoelectric ceramic plates 5, 5, while the other of the external lead electrodes 4a, 4b is connected to the other of the signal pickup electrodes 6, 6.

The operation of the described acceleration sensor 1 is as follows. It is assumed that the central portion of the piezoelectric element 2 is mainly deflected to be convex upward as illustrated in FIG. 3, in response to an acceleration G. In such a case, positive (+) charges are generated on the outer surface of the central section 5a of the piezoelectric ceramic plate 5 which is on the outer side as viewed in the direction of deflection of the piezoelectric element 2, based on the relationship between the direction A of polarization and the tensile stress Pt. Similarly, positive charges are generated on the outer surfaces of both end sections 5b, 5b of the same piezoelectric ceramic plate 5, due to the relationship between the direction B of polarization and the compression stress Pc.

The positive charges generated on the outer major surfaces of the central section 5a and both end sections 5b, 5b of the above-mentioned piezoelectric ceramic plate 5 are delivered from the signal pickup electrode 6 to the associated external lead electrode 4b while being summed with each other.

In the meantime, negative (−) charges are generated on the outer surface of the central section 5a of the piezoelectric ceramic plate 5 which is on the inner side as viewed in the direction of deflection of the piezoelectric element 2, based on the relationship between the direction C of polarization and the Compression stress Pc. Similarly, negative charges are generated on the outer surfaces of both end sections 5b, 5b of the same piezoelectric ceramic plate 5, due to the relationship between the direction D of polarization and the compression stress Pt. These negative charges are transferred to external lead electrodes 4a from the signal pickup electrode 6 associated with this piezoelectric ceramic plate 5.

Although negative charges and positive charges are generated on the inner surfaces of the piezoelectric ceramic plates 5, 5, respectively, the negative charges and the positive charges cancel each other via the intermediate electrodes 7, 7.

A description will now be given as to why tension and compression are applied to the piezoelectric ceramic plates 5, 5 of the piezoelectric element 2 in response to the action of the acceleration G. When the whole acceleration sensor 1 is accelerated by the acceleration G, such an acceleration directly acts on the package 3 tending to move the package 3 in the direction of the acceleration G. However, the piezoelectric element 2 is not directly subjected to such an acceleration so that the piezoelectric element 2 tends to remain in the state before the application of the acceleration. Namely, inertia force is generated in response to the acceleration G so as to act on the piezoelectric element 2. The end sections 5b, 5b of both piezoelectric ceramic plates 5, 5 tend to move together with the package 3 by being pulled by the package 3, whereas the central sections 5a, 5a tend to remain at their original position, whereby the central portion of the piezoelectric element 2 is mainly deformed to deflect in the direction opposite to that of action of the acceleration G, such as to be convex upward in the illustrated case. As a consequence, tensile stress Pt is generated in the central section 5a of the piezoelectric ceramic plate 5 which is on the outer side of the deflection, i.e., the upper piezoelectric ceramic plate 5, while compression stress Pc is generated in each of the end sections 5b of the same piezoelectric ceramic plate 5, as will be seen from FIG. 3. Conversely, the piezoelectric ceramic sheet 5 which is on the inner side of the deflection, i.e., the lower piezoelectric ceramic plate 5, is stressed such that compression stress Pc appears in the central section 5a, while tensile stress Pt appears in each of the end sections 5b, 5b of this piezoelectric ceramic plate 5.

The acceleration sensor 1 which has been described is mounted on a printed circuit board 12 such that one of the four major surfaces is directed upward, depending on the direction of sensitivity axis according to the design requirement, in a manner as shown in FIG. 4(a) or a manner as shown in FIG. 4(b). Thus, the direction of the sensitivity axis is determined by the posture of the piezoelectric sensor 1 on the circuit board. Turning sideways or other movement of the acceleration sensor 1 during soldering due to lack of stability is avoided regardless of the posture of the piezoelectric sensor. In FIGS. 4(a) and 4(b), numerals 1a and 1b denote upper and lower surfaces, while numerals 1c and 1d represent right and left side surfaces. When the piezoelectric sensor 1 is mounted in a manner shown in FIG. 4(a), the axis of sensitivity extends in the direction parallel to the printed circuit board 12 as indicated by the arrow, whereas, when the same is mounted in the posture as shown in FIG. 4(b), the axis of sensitivity extends in the direction perpendicular to the plane of the printed circuit board 12.

A process for packaging the acceleration sensor 1 typically employs a tape carrier 20. FIG. 5 shows such a tape carrier 20 by way of example. The tape carrier 20 is adapted to hold a plurality of independent acceleration sensors 1 of the type described above. More specifically, the tape carrier 20 has an embossed tape 21 having substantially square recesses 23 approximating the configuration of the acceleration sensor 1, at a predetermined pitch along the length thereof, and an upper tape 22 which is bonded to the upper side of the embossed tape 21 so as to close the above-mentioned recesses 23. All the acceleration sensors 1 on the same tape carrier 20 are disposed in the same posture in regard to the axis of sensitivity as indicated by arrows, depending on the direction of sensitivity axis to be obtained when these sensors 1 are mounted on circuit boards or the like. For instance, the posture in which the acceleration sensors 1 are accommodated in the recesses 23 of the tape carrier 20 is determined such that the left side surface id of each acceleration sensor 1 is exposed through an opening of the recess 23 in the tape carrier 20.

Preparation of a plurality of acceleration sensors on the tape carrier 20 in the described manner facilitates packaging of the sensors 1 on the printed circuit boards. Namely, the packaging can be performed by a simple process having the steps of peeling the upper tape 22 off the tape carrier 20 so as to expose one surface of the acceleration sensor 1 in each recess 23, picking up the acceleration sensor 1 by, for example, a vacuum sucker (not shown) acting on the exposed surface of the acceleration sensor 1, and placing the acceleration sensor 1 on the target position on the printed circuit board.

The described embodiment is only illustrative and various changes and modifications may be made thereto. For instance, the piezoelectric element 2 may be a so-called uni-morph type element which is cantilevered by the clamping members 8, 9 at its one end, rather than being supported at both its longitudinal ends as in the described embodiment. Furthermore, the piezoelectric element 2 may be constructed to serve as a vibration sensor, although an acceleration sensor has been specifically mentioned.

In the illustrated embodiment, each external lead electrode 4 is formed to cover not only each end surface of the package but also the portion of the peripheral surface of the package near each longitudinal end of the package 3. The external lead electrode 4, however, may be formed to cover only each end surface of the package 3.

Furthermore, the directions of polarizations of the sections of the piezoelectric ceramic plates 5 may be determined such that the directions A and C of polarizations of the central sections 5a, 5a are away from each other, while the directions B and D of polarizations of the end sections 5a, 5a; 5a, 5a are towards each other.

Second Embodiment

The acceleration sensor 1 described as the first embodiment of the present invention has a square cross-section perpendicular to the longitudinal axis. It is therefore impossible to discriminate the direction of the sensitivity axis based on the appearance. This poses a risk that the acceleration sensor 1 when mounted on a printed circuit board, for example, is placed in a wrong posture. Such a risk can be overcome when the acceleration sensor 1 of the first embodiment is mounted on the circuit board in accordance with a method which will be described hereinunder. With this method, it is possible to mount the acceleration sensor 1 such that the sensitivity axis is extended in the desired direction without fail, so that the advantage of the acceleration sensor, which resides in alternative posture of mounting, can be fully enjoyed.

Figure 7:
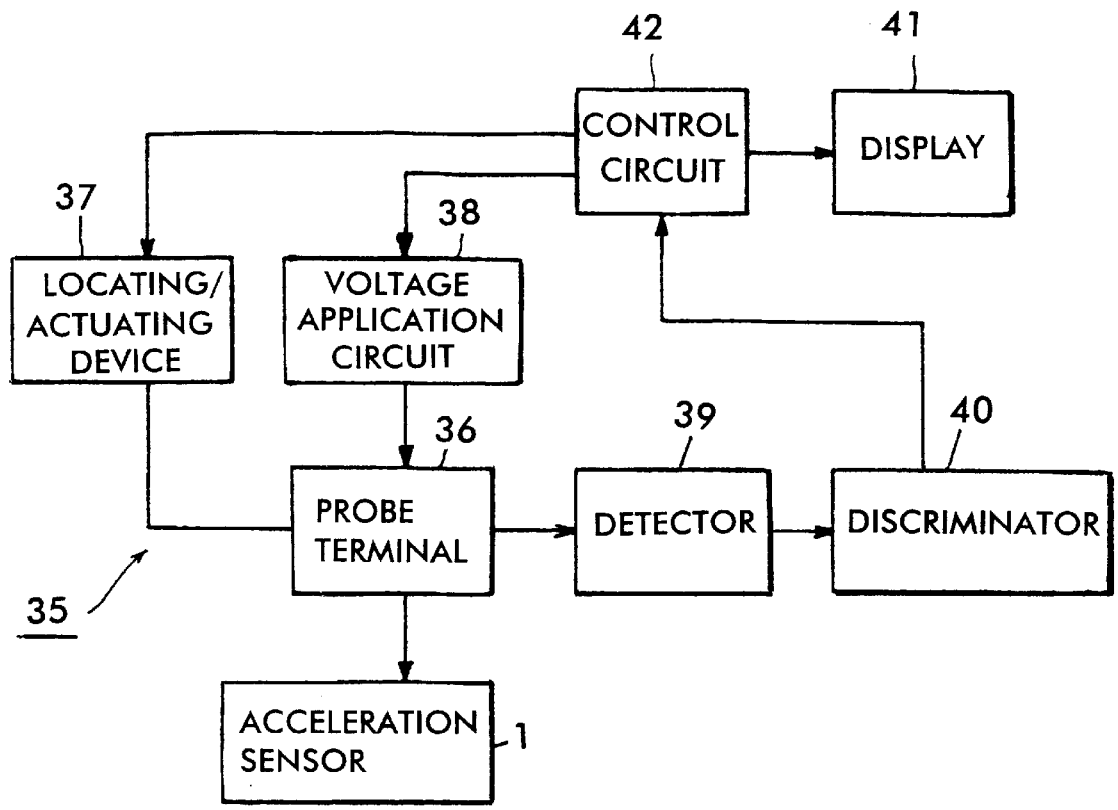
FIG. 7 is a block diagram schematically showing the construction of an examining device used in combination with the acceleration sensor of the second embodiment.

Although the acceleration sensor of the first embodiment is specifically mentioned in the following description, it is to be noted that the following method can be carried out by using other types of electronic parts. FIGS. 6(a) to 6(d) are perspective views of the acceleration sensor, while FIG. 7 is a block diagram schematically showing the construction of an acceleration sensor examining device.

Although not shown, the acceleration sensor 1 has a piezoelectric element arranged in a manner like a bridge and packaged in an insulating package which has a rectangular parallelopiped configuration. The direction of the axis of sensitivity varies as indicated by arrows depending on the posture of the piezoelectric element in the sensor. When the acceleration sensor is placed in the posture as shown in FIG. 6(a), the axis of sensitivity extends in the horizontal direction.

External lead electrodes 32, 33 for delivering voltages of opposite polarity, i.e., positive and negative voltages, are provided in the form of layers laid on both longitudinal ends of the acceleration sensor 1. More particularly, the external lead electrode 32 is laid on the front end surface 31a of the acceleration sensor 1 and the regions of the upper, lower, left and right surfaces 31c to 31f adjacent to the front end surface 31a of the sensor 1. Likewise, the external lead electrode 33 is laid on the rear end surface 31b and the regions of the upper, lower, left and right surfaces 31c to 31f adjacent to the rear end surface 31b of the sensor 1. More specifically, the external lead electrode 32a on the front end surface 31a delivers a voltage of positive polarity, while the external lead electrode 33 on the rear end surface 31b delivers a voltage of negative polarity. A dummy electrode 34 formed of a web-like conductive film is provided on the upper surface 31c among the surfaces 31c to 31f, at a predetermined position closer to the positive external lead electrode 32 than to the negative external lead electrode 33. The dummy electrode 34 extends over the entire width of the upper surface 31c and has a size large enough to allow a pair of probe terminals 36 to contact therewith for the purpose of applying a voltage which will be described later. The dummy electrode 34 serves as a sign indicating that the acceleration sensor 1 should be mounted on, for example, a printed circuit board (not shown) in such a posture that the surface in which the dummy electrode 34 is present is directed upward, and the surface on which this dummy electrode is provided is determined depending on factors such as the direction of the sensitivity axis, polarities of the external lead electrodes 32, 33, and so forth. The dummy electrode 34 may be formed, for example, by firing with silver, application of a conductive paste or by plating.

Whether the acceleration sensor 1 has been situated in correct posture is examined before the sensor 1 is packaged on, for example, a printed circuit board. The examination is conducted by using an examination device 35 which will now.be described with reference to FIG. 7.

The examination device 35 has a pair of probe terminals 36 for applying a voltage, locating/actuating device 37 for locating the probe terminals 36 both in vertical and horizontal directions, voltage application circuit 38 for applying a predetermined voltage to the probe terminal 36, detector 39 for detecting any electrical current between the probe terminals 36, discriminator 40 for discriminating whether or not the acceleration sensor 1 is in correct posture, based on the results of detection performed by the detector 39, display 41 for displaying the results of the discrimination performed by the discriminator 40, and control circuit 42 for controlling the operations of the described components in order to execute the examination processing. The detector 39, which is in this embodiment a current-sensitive detector, may be of the type which senses resistance or capacitance. When such a detector is used, the discriminator 40 performs the discrimination based on the results of comparison between the detected value and a predetermined reference value.

Using the examination device 35 having the described construction, an examination as to whether the acceleration sensor 1 is in correct posture or not is examined in accordance with the following procedure.

The acceleration sensor 1 as the examination object is placed in a predetermined posture in regard to up and down, left and right and front and back directions. When the posture of the acceleration sensor 1 is correct, the upper surface 31c, i.e., the surface carrying the dummy electrode 34, is directed upward and, when the sensor 1 in such a posture is viewed in top plan view, the front end surface 31a is directed to the south and the rear end surface 31b is directed to the north, with the left and right side surfaces 31e and 31f respectively directed to the east and west. Thus, the dummy electrode 34 is positioned closer to the south end of the sensor than to the north end.

The probe electrodes 36 are brought into contact with the acceleration sensor 1. Namely, the locating/actuating device 37 is activated to move the probe electrodes 36 to an area where the acceleration sensor 31 is disposed. More specifically, the probe electrodes 36 are moved to and located at a position where the dummy electrode 34 should exist when the acceleration sensor 31 is disposed in the correct posture, and are further moved into contact with the dummy electrode 34.

Then, a predetermined voltage is applied between the probe electrodes 36 across the sensor 1 so as to detect any electrical current flowing between the probe electrodes 36.

If the acceleration sensor 1 is in the correct posture as shown in FIG. 6(a), the probe electrodes 36 safely contact with the dummy electrode 34 so that an electrical current flows between the probe electrodes 36 through the dummy electrode 34 so as to be detected by the detector 39. In response to the output from the detector 39, the discriminator 40 determines that the acceleration sensor 1 is in the correct posture, and the control circuit 42 gives instruction to the display 41 to cause the latter to display that the examined acceleration sensor 1 is in the correct posture.

However, if the acceleration sensor 1 is in a wrong posture, e.g., turned upside down, falls sideways or rotated such that the front end surface is directed improperly, as shown in FIGS. 6(b) to 6(d), no electrical current flows between the probe electrodes 35 because these electrodes do not contact with the dummy electrode 34 on the acceleration sensor 1. When no electrical current is detected by the detector 39, the discriminator 40 determines that the acceleration sensor 1 is in a wrong posture, so that the control circuit 42 gives instruction to cause the display 41 to display that the examined acceleration sensor 1 is in the wrong posture.

The operator monitors the display on the display 41 to check whether each acceleration sensor is in the correct posture. When the acceleration sensor has been placed in the correct posture, the assembly process advances to the next step for soldering, otherwise the process skips to a step in which an operation is performed to correct the posture of the acceleration sensor 1. Although in the described embodiment, display 41 is employed to display the results of the examination, such a display operation is not essential. Namely, one of the above-mentioned two steps may be automatically selected in accordance with the output from the discriminator.

Thus, the examination device 35 is required only to perform a two-step operation applying a voltage through the probe terminals 36 and discriminating presence or absence of electrical current flowing between the probe terminals 36. Thus, the described examination device 35 handles much less amount of data as compared with known examination apparatus which rely on image processing techniques, whereby the costs of the facility for the examination are greatly reduced. In addition, examination is performed with a higher degree of reliability than by manual inspection and makes it possible to realize an inexpensive examination system incorporated in an automatic production line.

The dummy electrode 34 on the acceleration sensor 1 can be formed simultaneously with the formation of the external lead electrode 32, 33, without requiring any additional step in the production process, so that cost of production of the acceleration sensor 1 is not substantially raised.

The described embodiments are only illustrative and various changes and modifications may be made thereto.

Firstly, it is to be noted that the square cross-section of the acceleration sensor is not essential and other cross-sectional shapes also may be employed. For instance, acceleration sensors as modifications which will now be described have a rectangular cross-section perpendicular to the longitudinal axis.

Figure 8:
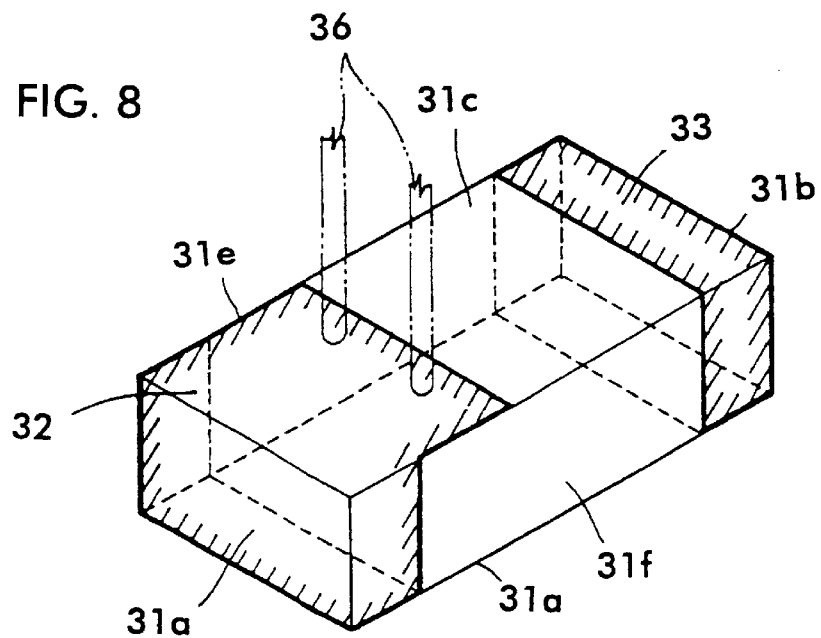
FIG. 8 is a perspective view of a modification of the acceleration sensor.
Figure 9:
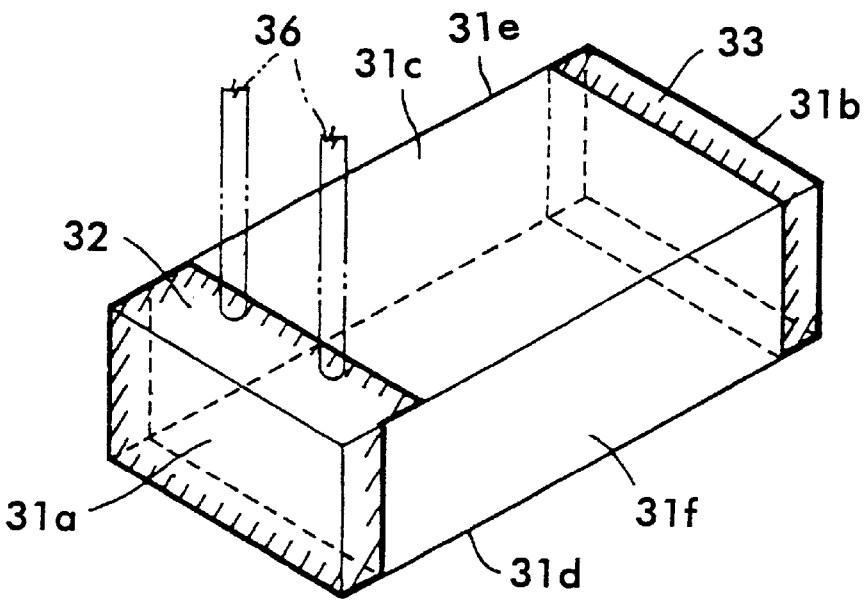
FIG. 9 is a perspective view of another modification of the acceleration sensor.
Figure 10:
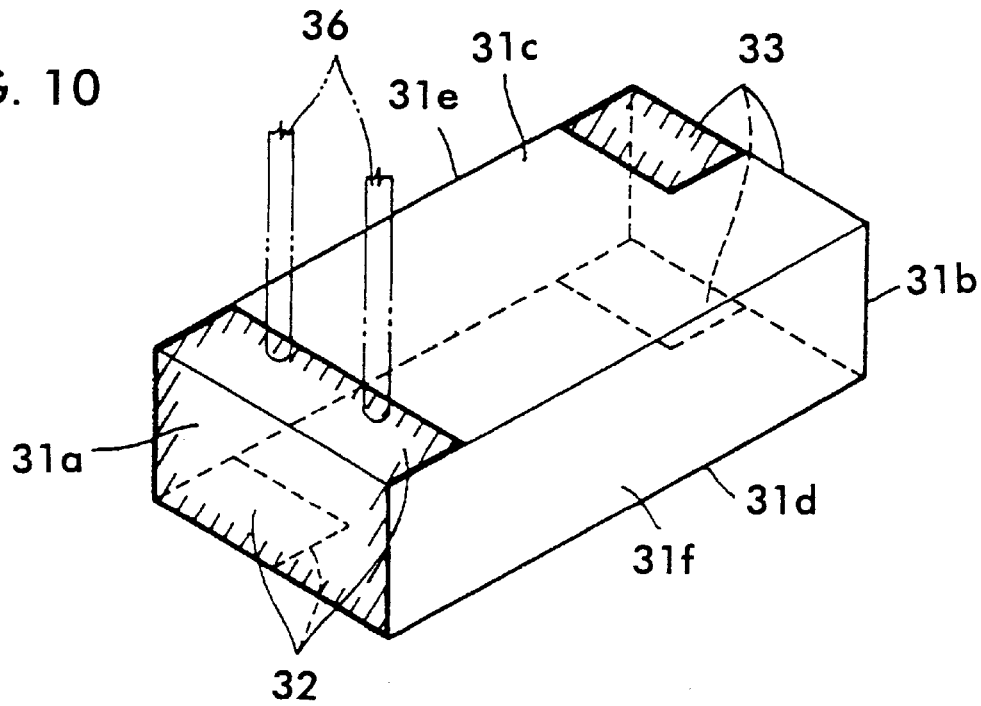
FIG. 10 is a perspective view of still another modification of the acceleration sensor.

In these modifications, the positive external lead electrode 32 and the negative external lead electrode 33 provided on the acceleration sensor 1 are made to have different areas as shown in FIGS. 8 to 10 so as to provide information as to the posture, instead of the dummy electrode 34 used in the described embodiments.

More specifically, FIG. 8 shows a modification in which the portion of the positive external lead electrode 32 on the upper surface 31c of the acceleration sensor 1 is extended to a region contactable with the probe electrodes 36, whereas the size and area of the portions of the external lead electrode 32 on the lower surface 31d and left and right side surface 31e, 31f, as well as the size and area of the negative external lead electrode 33 on all the surfaces 31c, 31d, 31e and 31f, are so designed that these portions are not extended to regions contactable with the probe electrodes 36.

In the modification shown in FIG. 9, the portion of the external lead electrode 32 on the upper surface 31c is extended to the same length as that in the first embodiment, but the portions of this electrode 32 on the lower surface 31d and left and right side surfaces 31e, 31f, as well as the portions of the negative external lead electrode 33 on all the surfaces 31c, 31d, 31e and 31f, are retracted so as not to be contacted by the probe terminals 36.

In the modification shown in FIG. 10, the portion of the positive external lead electrode 32 on the upper surface 31c of the acceleration sensor 1 has the same size and area as that in the embodiment shown in FIG. 9, whereas the portions of the positive and negative external lead electrodes 32, 33 on both side surfaces 31e, 31f are omitted. The portion of the positive external lead electrode 32 on the lower surface 31d, as well as the portions of the negative external lead electrodes 33 on the upper and lower surfaces 31c, 31d, is formed to extend over only half the width of the acceleration sensor 1 so as not to be simultaneously contacted by two probe electrodes 36.

Each of the modifications shown in FIGS. 8 to 10 can be examined by using the examination device 35 described before. Examinations of the modifications shown in FIGS. 9 and 10, however, require that the positions at which the probe terminals 36 contact the acceleration sensor are shifted from that in the cases shown in FIGS. 6(a)–6(d) and 8.

Although in the described embodiments the external lead electrodes 32, 33 are formed to cover not only the longitudinal front and rear end surfaces 31a, 31b but also portions of the upper, lower, left and right surfaces 31c to 31f adjacent to the respective end surfaces, the present invention does not exclude such an arrangement that the external lead electrodes 32, 33 are formed to cover only the front and rear end surfaces 31a, 31b.

Figure 11:
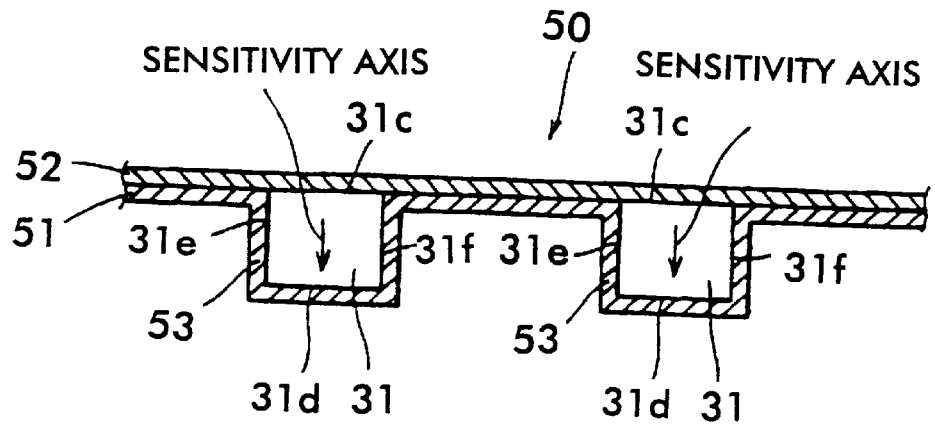
FIG. 11 is an illustration of an acceleration sensor carried by a tape carrier.

In the embodiment described in connection with FIGS. 6(a) to 10, the examination device 35 is used for the purpose of examining the posture of the acceleration sensor 1 in the course of mounting of the sensor on a printed circuit board. The same examination device 35 also can be used for the purpose of examining the posture of the acceleration sensor 1 when the sensor 1 is loaded on a tape carrier 50 as shown in FIG. 11 which is used, as explained before, for the purpose of conveying a plurality of acceleration sensors 1.

The tape carrier 50 is adapted to hold a plurality of independent acceleration sensors 1 of the type described above. More specifically, the tape carrier 50 has an embossed tape 51 having substantially square recesses 53 approximating the configuration of the acceleration sensor 1, at a predetermined pitch along the length thereof, and an upper tape 52 which is bonded to the upper side of the embossed tape 51 so as to close the above-mentioned recesses 53. All the acceleration sensors 1 on the same tape carrier 50 are disposed in the same posture in regard to the axis of sensitivity, depending on the direction of sensitivity axis to be obtained when these sensors 1 are mounted on a circuit boards or the like. For instance, the posture in which the acceleration sensors 1 are accommodated in the recesses 53 of the tape carrier 50 is determined such that the upper surface 31c of each acceleration sensor 1 is exposed through the opening of the recess 23 in the tape carrier 50. Loading of the acceleration sensors 1 in the predetermined posture on the tape carrier 50 can be executed advantageously and effectively by using the examination device 35 which is capable of ascertaining that the acceleration sensors 1 have been placed in the correct posture.

Third Embodiment

Figure 12:
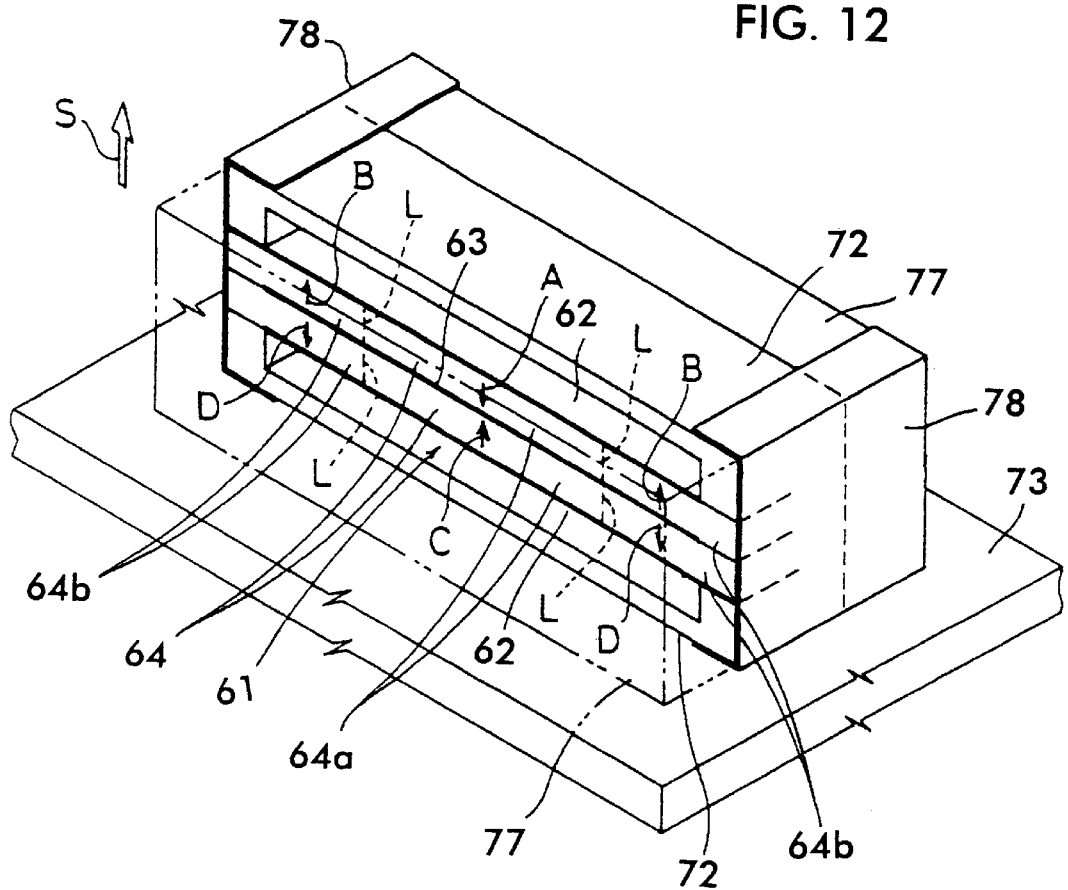
FIG. 12 is a schematic sectional perspective view of the third embodiment of the acceleration sensor.

A third embodiment of the acceleration sensor in accordance with the present invention will now be described with reference FIG. 12, which is a schematic perspective view of a third embodiment, FIG. 13 which is a schematic illustration of deformation of a bimorph element under acceleration, and FIG. 14 which is a schematic illustration of the acceleration sensor deformed due to deflection of a circuit board.

The third embodiment of the acceleration sensor is adapted to be packaged on the surface of a circuit board 7 after being correctly located. The acceleration sensor has a bimorph element 61 having a highest sensitivity axis S extending in a direction substantially normal to the surface of the circuit board, a pair of end case members 72 which support both longitudinal end portions of the bimorph element 61 by clamping these ends at the upper and lower surfaces of the bimorph element 61, and a pair of side case members 77 which is integrated with the end case members 72 while sealing both longitudinal side surfaces of the bimorph element 61.

The bimorph element 61 has a pair of strip-like piezoelectric ceramic plates 64, 64 each having a thin-film signal electrode 62 and a thin-film intermediate electrode 63 formed on the opposite major surfaces thereof, the piezoelectric ceramic plates 64, 64 being joined together at their surfaces having the intermediate electrodes 63. Each piezoelectric ceramic plate 64 is divided into three sections along the length thereof: namely a central section 64a and both end sections 64b, 64b at a pair of border lines L, L. The positions of the border lines L, L are so determined that, when the bimorph element 61 has been deformed due to a deflection of the circuit board 73, the quantity of the charges generated in the central section 64a equals to the sum of the quantities of charges generated in both end sections 64b, 64b. The central section 64a and both end sections 64b, 64b have been polarized thicknesswise of the ceramic plate 64 in opposite directions as indicated by arrows A and B. Similarly, the other piezoelectric ceramic plate 64 also is sectioned into a central section 64a and end sections 64b, 64b, and these sections are polarized thicknesswise in the directions opposite to those of the corresponding sections of the first-mentioned piezoelectric ceramic plate 64, as indicated by arrows C and D, respectively. Thus, the central sections 64a, 64a of both piezoelectric ceramic plates 64, 64 of the bimorph element 61 are polarized inward, i.e., towards each other, as indicated by arrows A and C in FIG. 12, whereas both end sections 64b, 64b; 64b, 64b of both piezoelectric ceramic plates 64, 64 are polarized outward, i.e., away from each other, as indicated by arrows B and D. One of the pair of signal electrodes 62 presented on the outer surfaces of the piezoelectric ceramic plates 64, 64 is connected to an external lead terminal 78 which covers one longitudinal end of the case assembly 72, 77, while the other of the signal electrodes 62 is connected to an external lead terminal 78 which covers the other end of the case assembly 72, 77. The acceleration sensor thus constructed senses acceleration based on the quantity of charges generated by the bimorph element 61.

Figure 13:
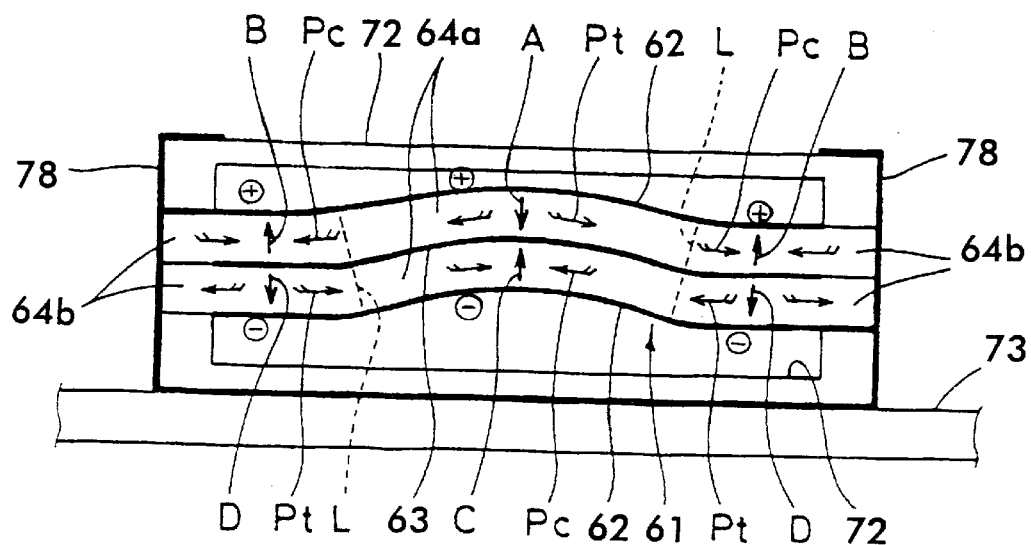
FIG. 13 is an illustration of a bimorph element deformed under action of an acceleration.

Deformation of the bimorph element 61 under acceleration mainly appears in the central section 64a as schematically shown in FIG. 13. In each of the piezoelectric ceramic plates 64, 64 forming the bimorph element 13, tensile stress is generated in the central section 64a, while both end sections 64b, 64b sustain compression stress Pc. However, since the central section 64a and both end sections 64b, 64b of each piezoelectric ceramic plate 64 are polarized in opposite directions, charges generated in the central section 64a due to tensile stress Pt and charged generated in both end sections 64b, 64b due to compression stress Pc are not canceled by each other, so that the bimorph element 61 produces a large quantity of charges, i.e., a high level of output signal.

More specifically, in the piezoelectric ceramic plate 64 which is on the outer side of the bimorph element 61 as viewed in the direction of the deflection, i.e., the upper piezoelectric ceramic plate 64, positive (+) charges are generated on the outer major surface of the central section 64a based on the relationship between the polarization direction A and the tensile stress Pt. Positive charges are also generated on the outer major surfaces of both end sections 64b, 64b of the same piezoelectric ceramic plate 64, based on the relationship between the polarization direction B and the compression stress Pc. Consequently, the positive charges generated on the outer major surface of the central section 64a and the positive charges generated on the outer major surfaces of both end sections 64b, 64b are transferred from the signal electrode 62 to the associated external lead electrode 78 while being summed with each other.

In the meantime, negative (−) charges are generated in the piezoelectric ceramic plate 64 which is on the inner side of the acceleration sensor 1 as viewed in the direction of deflection, i.e., in the lower piezoelectric ceramic plate 64. More specifically, negative (−) charges are generated in the outer major surface of the central section 64a of this piezoelectric ceramic plate 64, due to the relationship between the polarization direction C and the compression stress Pc. Negative charges are also generated in the outer major surfaces of both end sections 64b, 64b of this piezoelectric ceramic plate 64, due to the relationship between the polarization direction D and the tensile stress Pt. The negative charges generated on the central section 64a and the negative charges generated on both end sections 64b, 64b are transferred from the signal electrode 62 to the associated external lead terminal 68 while enhancing each other. Consequently, large quantities of positive and negative charges are generated in the bimorph element 61 so that a high level of sensor output is derived from this acceleration sensor.

In each of the piezoelectric ceramic plates 64, 64 under acceleration, charges of polarity opposite to that of the charges produced on the outer major surface are generated on the inner major surface, i.e., on the surface facing the other piezoelectric ceramic plate 64. These charges on the inner major surfaces of both piezoelectric ceramic plates 64, 64 are of opposite polarities and, hence, cancel each other through the electrical connection between the intermediate electrodes 63, 63 on these piezoelectric ceramic plate 64, 64.

Figure 14:
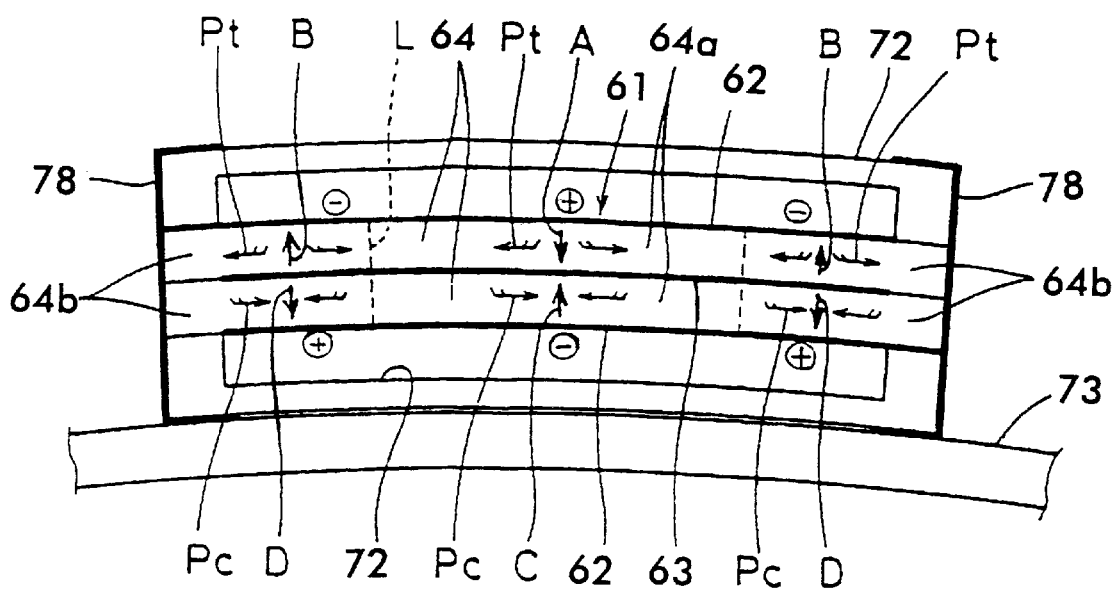
FIG. 14 is a schematic. illustration of an acceleration sensor deformed due to deflection of a circuit board.

FIG. 14 schematically shows the state in which a circuit board 13 on which the acceleration sensor is mounted has been deflected or a circuit board 73 after the mounting of the acceleration sensor is deflected, so as to cause a deformation of the whole bimorph element 61. Note that the deflection of the circuit board 73 deforms the whole bimorph element 61, while the deformation of the bimorph element 61 under acceleration mainly appears in the central section 64a as schematically shown in FIG. 13.

In such a case, tensile stresses Pt are generated in all the sections 64a, 64b, 64b of the ceramic plate 64 which is on the outer side of the bimorph element 61 as viewed in the direction of the deflection, while compression stresses Pc are generated in all the sections 64a, 64b, 64b of the piezoelectric ceramic plate 64 which is on the inner side of the bimorph element 61 as viewed in the direction of the deflection. As a result, positive charges and negative charges are generated on the outer surfaces of section 64a and sections 64b, respectively, of the piezoelectric ceramic plate 64 which is on the outer side of the bimorph element 61 as viewed in the direction of the deflection. Moreover, negative charges and positive charges are generated on the outer surfaces of section 64a and sections 64b, respectively, of the piezoelectric ceramic plate 64 which is on the inner side of the bimorph element 61 as viewed in the direction of the deflection.

As is explained above, since the piezoelectric ceramic plates 64, 64 are divided into the central sections 64a and the end sections 64b, 64c so that the amount of the charges generated in the central section 64a equals to the sum of the amount of the charges generated in both end sections 64b, 64b, the charges generated in response to the deformation of the bimorph element 61 cancel each other, so that no electrical signal is derived from the acceleration sensor based on the deformation of the bimorph element caused by deflection of the circuit board. Accordingly, in the case where the bimorph element 61 deflected due to the deflected circuit board is also subject to an acceleration, the bimorph element 61 can output signals only in response to the acceleration, and detect the degree of acceleration correctly.

Although the invention has been described through its specific form, it is to be noted that the described embodiment is only illustrative and may be changed or modified within the scope of the invention which is limited solely by the appended claims.

What is claimed is:

1. An acceleration sensor comprising:
a bimorph element having an axis of highest sensitivity extending in a direction which substantially coincides with a line normal to the plane of a circuit board; and
a case assembly for fixing and supporting both longitudinal ends of said bimorph element, said case assembly being adapted to be mounted on said circuit board at both its longitudinal ends which are in support of both said longitudinal ends of said bimorph element;
wherein said bimorph element comprises a pair of piezoelectric ceramic plates each having a signal electrode and an intermediate electrode formed on opposite major surfaces thereof, said piezoelectric ceramic plates being joined to each other face to face at the surfaces having said intermediate electrodes such that said intermediate electrodes are coupled to each other;
each said piezoelectric ceramic plate having sections in the longitudinal direction of said bimorph element, there being three sections including a central section and an end section at each end of the central section, the sections being positioned such that, when said bimorph element is deformed in response to deflection of said circuit board, a quantity of charges is generated in said central section equal to a sum of the quantities of charges generated in both said end sections, said central section and both said end sections of each said piezoelectric ceramic plate being polarized thicknesswise of said piezoelectric ceramic plate in opposite directions of polarization, the directions of polarization of said central section and both said end sections of one of said piezoelectric ceramic plates being opposite to those of the other of said piezoelectric ceramic plates.

2. A piezoelectric sensor, comprising:
a piezoelectric element having a specific axis of sensitivity and detecting an acceleration along said specific axis; and
a package in which said piezoelectric element is provided;
wherein said package has a rectangular parallelopiped configuration comprising four major surfaces with end surfaces having a height-to-width ratio approximating 1:1, wherein external lead electrodes are formed on at least said end surfaces, and wherein said package is mountable on a surface of a circuit board such that any one of said four major surfaces may be mounted on the circuit board;
wherein said piezoelectric element comprises a pair of strip-shaped piezoelectric ceramic plates each having on its major surfaces a signal pickup electrode and an intermediate electrode, and said pair of strip-shaped piezoelectric ceramic plates is joined face to face at the intermediate electrodes thereof;
and further wherein each of the strip-shaped piezoelectric ceramic plates is divided into a center section and two end sections interposing said center section, and said center section is polarized in a direction opposite to that of said end sections.

3. A piezoelectric sensor, comprising:
a piezoelectric element having a specific axis of sensitivity and detecting an acceleration along said specific axis; and a package in which said piezoelectric element is provided;

wherein said piezoelectric element has a pair of strip-shaped piezoelectric ceramic plates joined to each other, and said package includes a pair of clamping members for clamping at least one longitudinal end of said piezoelectric element from the upper and lower sides thereof so as to support said piezoelectric element, and a pair of side cover members secured to both sides of said clamping members so as to cover left and right side surfaces of said piezoelectric element; and wherein said package has a substantially rectangular parallelopiped configuration comprising four major surfaces with end surfaces having a height-to-width ratio approximating 1:1, and external lead electrodes are formed on at least said end surfaces, and wherein said package is mountable on a surface of a circuit board such that any one of said four major surfaces may be mounted on the circuit board;

wherein said piezoelectric element comprises a pair of strip-shaped piezoelectric ceramic plates each having on its major surfaces a signal pickup electrode and an intermediate electrode, and said pair of strip-shaped piezoelectric ceramic plates is joined face to face at the intermediate electrodes thereof;

and further wherein each of the strip-shaped piezoelectric ceramic plates is divided into a center section and two end sections interposing said center section, and said center section is polarized in a direction opposite to that of said end sections.

\* \* \* \* \*